United States Patent
Johnson et al.

(10) Patent No.: US 11,638,833 B2
(45) Date of Patent: *May 2, 2023

(54) REDUCING LIGHT POLUTION IN PHOTOBIOMODULATION THERAPY OF A PATIENTS EYE

(71) Applicant: MULTI RADIANCE MEDICAL, Solon, OH (US)

(72) Inventors: Douglas Johnson, Brownstown, MI (US); Max Kanarsky, Solon, OH (US); Larry W. Finn, Georgetown, TX (US); Ian Dwayne Campbell, Saginaw, TX (US); Jeffrey A. Lenk, Hutto, TX (US); Michael T. Barrett, Georgetown, TX (US); Scott R. Lenk, Taylor, TX (US)

(73) Assignee: MULTI RADIANCE MEDICAL, Solon, OH (US)

( * ) Notice: Subject to any disclaimer, the term of this patent is extended or adjusted under 35 U.S.C. 154(b) by 378 days.

This patent is subject to a terminal disclaimer.

(21) Appl. No.: 16/936,597

(22) Filed: Jul. 23, 2020

(65) Prior Publication Data
US 2020/0353282 A1  Nov. 12, 2020

Related U.S. Application Data

(63) Continuation-in-part of application No. 16/317,984, filed as application No. PCT/US2018/044954 on Aug. 2, 2018, now Pat. No. 10,744,341.
(Continued)

(51) Int. Cl.
*A61N 5/06* (2006.01)
*A61N 5/067* (2006.01)

(52) U.S. Cl.
CPC ............ *A61N 5/0613* (2013.01); *A61N 5/067* (2021.08); *A61N 2005/0626* (2013.01);
(Continued)

(58) Field of Classification Search
CPC .................. A61N 5/0613; A61N 5/067; A61N 2005/0626; A61N 2005/0648;
(Continued)

(56) References Cited

U.S. PATENT DOCUMENTS 2,389,223 A * 11/1945 Werner ............ A61F 9/04
2/15
4,858,609 A    8/1989 Cole
(Continued)

FOREIGN PATENT DOCUMENTS

RU    2297813 C1    4/2007
WO    2008127204 A1   10/2008
(Continued)

OTHER PUBLICATIONS

International Search Report and Written Opinion dated Oct. 23, 2018 for Application No. PCT/US2014/044954.
(Continued)

*Primary Examiner* — Eugene T Wu
(74) *Attorney, Agent, or Firm* — Tarolli, Sundheim, Covell & Tummino LLP

(57) ABSTRACT

Disorders of the eye can be treated by photobiomodulation therapy (PBMT) delivered by a PBMT device. The PBMT device can be configured for placement directly over a patient's eye socket to deliver light into the patient's eye regardless of a position of the patient's eye, while preventing blue light from entering the patient's eye (e.g., due to a filter within the PBMT device and/or an opacity of the housing of the PBMT device). The PBMT device can be powered by a controller.

19 Claims, 5 Drawing Sheets

Related U.S. Application Data

(60) Provisional application No. 62/540,204, filed on Aug. 2, 2017.

(52) U.S. Cl.
CPC ............. *A61N 2005/0648* (2013.01); *A61N 2005/0652* (2013.01); *A61N 2005/0659* (2013.01); *A61N 2005/0662* (2013.01); *A61N 2005/0667* (2013.01)

(58) Field of Classification Search
CPC .... A61N 2005/0652; A61N 2005/0659; A61N 2005/0662; A61N 2005/0667
See application file for complete search history.

(56) References Cited

U.S. PATENT DOCUMENTS

| | | | |
|---|---|---|---|
| 5,092,669 A * | 3/1992 | Anderson | G02C 5/001 351/203 |
| 5,568,208 A | 10/1996 | Van De Velde | |
| 5,755,752 A | 5/1998 | Segal | |
| 6,033,431 A | 3/2000 | Segal | |
| 6,254,596 B1 | 7/2001 | Lawandy | |
| 6,319,273 B1 | 11/2001 | Chen | |
| 6,385,221 B1 | 5/2002 | Neuberger | |
| 6,421,361 B1 | 7/2002 | Neuberger | |
| 6,507,758 B1 | 1/2003 | Greenberg | |
| 6,599,891 B2 | 7/2003 | North | |
| 6,648,876 B2 | 11/2003 | Murakami | |
| 6,676,655 B2 | 1/2004 | McDaniel | |
| 6,800,086 B2 | 10/2004 | Strong | |
| 6,808,523 B2 | 10/2004 | Fujisaka | |
| 6,986,782 B2 | 1/2006 | Chen | |
| 7,015,240 B2 | 3/2006 | North | |
| 7,018,395 B2 | 3/2006 | Chen | |
| 7,158,555 B2 | 1/2007 | Momiuchi | |
| 7,288,106 B2 | 10/2007 | Heacock | |
| 7,311,723 B2 | 12/2007 | Seibel | |
| 7,331,954 B2 | 2/2008 | Temelkuran | |
| 7,354,432 B2 | 4/2008 | Eells | |
| 7,479,136 B2 | 1/2009 | Dotson | |
| 7,682,027 B2 | 3/2010 | Buczek | |
| 7,744,590 B2 | 6/2010 | Eells | |
| 7,766,903 B2 | 8/2010 | Blumenkranz | |
| 7,794,453 B2 | 9/2010 | Zemmouri | |
| 7,883,535 B2 | 2/2011 | Cantin | |
| 7,980,745 B2 | 7/2011 | Shanbaky | |
| 7,991,258 B2 | 8/2011 | Temelkuran | |
| 8,105,321 B2 | 1/2012 | Zemmouri | |
| 8,109,981 B2 | 2/2012 | Gertner | |
| 8,180,444 B2 | 5/2012 | Neuberger | |
| 8,251,982 B2 | 8/2012 | Zaghetto | |
| 8,292,434 B2 | 10/2012 | Horvath | |
| 8,315,280 B2 | 11/2012 | Zimare | |
| 8,945,197 B1 | 2/2015 | Friend | |
| 9,592,404 B2 | 3/2017 | Dotson | |
| 2005/0237479 A1 * | 10/2005 | Rose | G02B 27/017 351/123 |
| 2005/0244469 A1 | 11/2005 | Whitcup | |
| 2006/0184214 A1 | 8/2006 | McDaniel | |
| 2007/0123844 A1 | 5/2007 | Henry | |
| 2008/0102122 A1 | 5/2008 | Mahadevan | |
| 2010/0241196 A1 * | 9/2010 | Meyer | G02B 3/08 607/88 |
| 2012/0088980 A1 | 4/2012 | Gravely | |
| 2013/0304162 A1 * | 11/2013 | Veres | A61N 5/0613 607/88 |
| 2013/0317570 A1 | 11/2013 | Luttrull | |
| 2014/0036511 A1 | 2/2014 | Whitfield | |
| 2014/0158541 A1 * | 6/2014 | Beaudet | G01N 27/44704 204/612 |
| 2015/0057701 A1 | 2/2015 | Kelleher | |
| 2016/0067086 A1 | 3/2016 | Tedford | |
| 2016/0067087 A1 | 3/2016 | Tedford | |
| 2016/0166853 A1 | 6/2016 | Dotson | |
| 2016/0270656 A1 * | 9/2016 | Samec | A61B 5/0059 |
| 2016/0317833 A1 | 11/2016 | Tedford | |
| 2016/0356475 A1 | 12/2016 | Honda | |
| 2017/0185042 A1 * | 6/2017 | Yuen | G04B 19/30 |

FOREIGN PATENT DOCUMENTS

| | | |
|---|---|---|
| WO | 2012123709 A1 | 9/2012 |
| WO | 2015011589 A1 | 1/2015 |
| WO | 2015073259 A3 | 5/2015 |
| WO | 2016049669 A1 | 4/2016 |
| WO | 2017004257 A1 | 1/2017 |

OTHER PUBLICATIONS

U.S. Appl. No. 13/679,557, filed Nov. 16, 2012, "Ophthalmic Phototherapy Device and Associated Treatment Method".
U.S. Appl. No. 15/050,484, filed Feb. 23, 2016, "Ophthalmic Phototherapy Device and Associated Treatment Method".
U.S. Appl. No. 15/050,483, filed Feb. 23, 2016, "Ophthalmic Phototherapy Device and Associated Treatment Method".
U.S. Appl. No. 15/050,482, filed Feb. 23, 2016, "Ophthalmic Phototherapy Device and Associated Treatment Method".
EP Search Report dated Jun. 24, 2020 for corresponding EP Application No. 18840919.7.

* cited by examiner

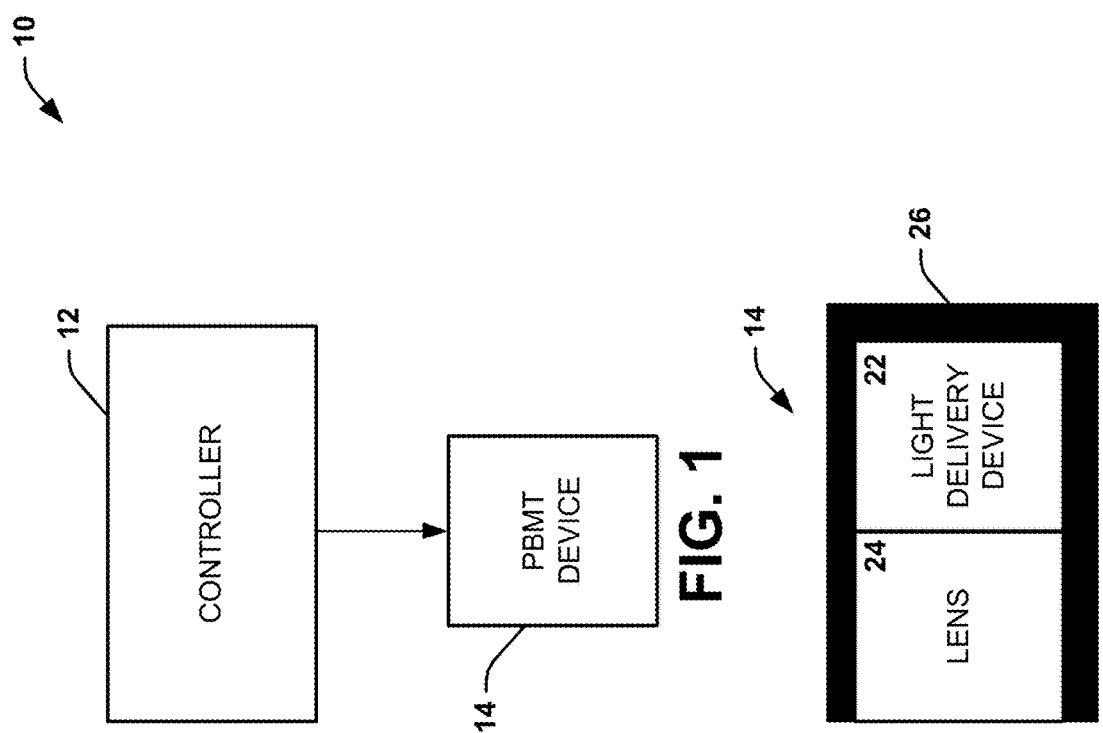

REDUCING LIGHT POLUTION IN PHOTOBIOMODULATION THERAPY OF A PATIENTS EYE

CROSS-REFERENCE TO RELATED APPLICATIONS

This application is a Continuation-in-Part of U.S. application Ser. No. 16/317,984, filed Jan. 15, 2019, which is a national stage entry of PCT Appl. No. PCT/US18/44954, filed Aug. 2, 2018, entitled "SYSTEM AND METHOD FOR DIRECTING LIGHT INTO A PATIENT'S EYE", which claims the benefit of U.S. Provisional Application No. 62/540,204, filed Aug. 2, 2017, entitled "SYSTEM AND METHOD FOR TREATMENT AND PREVENTION OF VISION DISORDERS USING LIGHT TREATMENT". This provisional application is hereby incorporated by reference in its entirety for all purposes.

TECHNICAL FIELD

The present disclosure relates generally to photobiomodulation therapy (PBMT) and, more specifically, to systems and methods that reduce light pollution in PBMT of a patient's eye.

BACKGROUND

White light is made up of rays from the entire visible spectrum (red, orange, yellow, green, blue, indigo, and violet), each with a different energy and wavelength. Rays on the red end of the visible spectrum have longer wavelengths and less energy. On the other end of the visible spectrum, blue rays have shorter wavelengths and more energy and are thought to be polluting the white light, and this pollution can be damaging to the eye and brain. Light that visibly appears white (e.g., sunlight, light from a computer screen, or the like) can be polluted with a large blue component. High energy blue light with a short wavelength (e.g., between 415 nm and 455 nm) can pass through the cornea and lens of the eye to the retina, leading to irreversible photochemical damage and even unintended neural stimulation. The entry of blue light into the eye is a risk of photobiomodulation therapy (PBMT) of the eye.

PBMT can be used to treat ocular disorders/diseases, like macular edema, cataract, disorders of tear glands, and the like. Macular edema causes distorted vision due to a buildup of fluid in the macula due to damaged blood vessels in the retina. However, traditional PBMT of the eye does not block white light from reaching the eye during the PBMT. Since traditional PBMT allows the large blue component of white light to reach the eye during the PBMT, the patient is at a risk for additional optical problems, potentially even caused by the treatment of the original optical disorder/disease.

SUMMARY

The present disclosure describes systems and methods that reduce light pollution in photobiomodulation therapy (PBMT) of a patient's eye.

In one aspect, the present disclosure can include a method for reducing light pollution in PBMT of the patient's eye when directing light into a patient's eye to treat a disorder of the eye. The method includes placing a PBMT device directly over a patient's eye socket to deliver light into the patient's eye, while preventing blue light from entering the patient's eye. The method can also include powering the light delivery devices to generate light; and directing the light into the patient's eye regardless of a position of the patient's eye wile preventing the blue light from entering the patient's eye.

In another aspect, the present disclosure can include a system that reduces light pollution in PBMT of the patient's eye when directing light into a patient's eye to treat a disorder of the eye. The system includes a PBMT device and a controller configured to power the PBMT device. The PBMT device can be configured for placement directly over a patient's eye socket to deliver light into the patient's eye, while preventing blue light from entering the patient's eye.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 1 is a block diagram illustration showing an example of a system that reduces light pollution in PBMT of the patient's eye when directing light into a patient's eye in accordance with an aspect of the present disclosure;

FIG. 2 is a block diagram illustration showing an example of the PBMT device of FIG. 1;

DETAILED DESCRIPTION

I. Definitions

Figure 3:
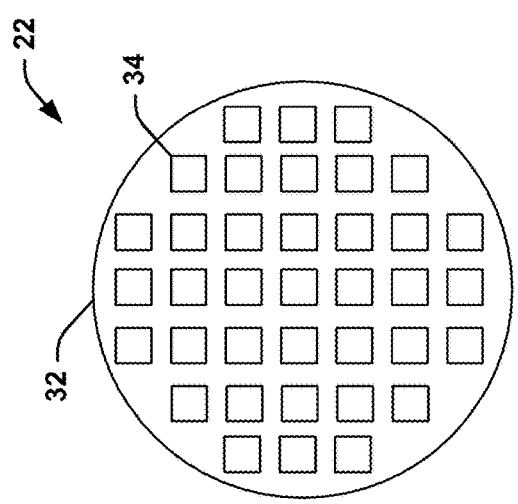
FIG. 3 is a block diagram illustration showing an example light delivery device of FIG. 2.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "light pollution" can refer to high energy, short wavelength blue light rays within white light. The blue light rays may have the potential to damage the eye.

As used herein, the term "eye" refers to an organ of sight. The eye has a number of components including, but not limited to, the cornea, iris, pupil lens, retina, macula, optic nerve, choroid, and vitreous. In some examples, when light is referred to as being directed through the eye, the light is directed into the pupil to reach the retina and/or macula. In other examples, when light is delivered into the patient's eye, the light can treat any part of the eye, including surrounding tear glands.

As used herein, the term "retina" refers to a nerve layer that lines the back of the eye, senses light and creates impulses that travel through the optic nerve to the brain. In other words, the retina receives light and converts the light to a neural signal.

As used herein, the term "macula" refers to a small area of the retina that contains special light-sensitive cells and allows for vision of fine details.

As used herein, the term "optic nerve" refers to the nerve that transmits visual information from the retina to the brain.

As used herein, the term "disorder of the eye" refers to any anatomic and/or functional pathological manifestation related to the eye that affects vision. Examples of disorders of the eye include, but are not limited to, macular degeneration, retinopathy, diabetic eye disease, optic neuropathy, amblyopia, induced retinal damage, and the like. Other examples include cataract, ocular surface disease (OSD), diseases or conditions affecting tear glands and/or causing dry eye, or the like.

As used herein, the term "photobiomodulation (PBM)" refers to the application of a light signal to a portion of a subject's body to induce a phototherapeutic response in cells within the portion of the subject's body.

As used herein, the term "photobiomodulation therapy (PBMT)" refers to a drug-free, non-invasive treatment procedure, in which a light signal is applied to the subject's eye to treat a certain medical condition (e.g., disorder of the eye).

As used herein, the terms "light" and "light signal" can be used interchangeably to refer to a treatment being delivered to a patient's eye. In some instances, the light/light signal can be white light. In other instances, the light/light signal can include one or more wavelengths from 500 nm to 1100 nm. However, the light may include a combination of wavelengths that create a synergistic effect when combined.

As used herein, the term "white light" can refer to electromagnetic radiation of all the frequencies in the visible range of the spectrum (including toxic blue light), appearing white to the eye. White light can come from, for example, sunlight, light from a television, light from a computer monitor, smartphone screen, tablet screen, light from compact fluorescent light bulbs, and the like.

As used herein, the term "blue light" can refer to blue-violet short-wave light in the visible spectrum. Blue light can be a significant part of white light and/or can be part of other types of light. As an example, blue light with wavelengths less than 455 nm (e.g., between 415 nm and 455 nm) can be toxic to the eye, causing dangerous light pollution.

As used herein, the term "printed circuit board" refers to a mechanism to mechanically support and electrically connect electrical components (like light delivery devices) using conductive tracks, pads, and other features etched from one or more sheet layers of a conductive material (like copper) laminated onto and/or between sheet layers of a non-conductive substrate. The printed circuit board can be rigid and/or flexible.

As used herein, the term "light delivery device" refers to an electrical component that can provide light at least one wavelengths upon receiving an electrical signal. For example, the light source can be a low-level laser source (e.g., a laser light emitting diode (LED)) that generates coherent light). As another example, the light source can be an incoherent light source, such as a traditional LED.

As used herein, the term "sufficient" refers to an amount adequate enough to satisfy a condition. For example, "a time sufficient to stimulate a phototherapeutic response in at least a portion of the eye" can refer to a light signal being applied to at least a portion of the eye for a time adequate enough to stimulate the phototherapeutic response.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure describes systems and methods that reduce light pollution in photobiomodulation therapy (PBMT) of a patient's eye. Light pollution generally refers to light rays on the blue-side of the visible spectrum with higher energy and lower wavelength. The polluting blue light is a large part of light that appears white, including sunlight, light from a television, light from a computer monitor, smartphone screen, tablet screen, light from compact fluorescent light bulbs, and the like (however, can be part of other types of light). The polluting blue light can cause symptoms from minor eye discomfort to major irreversible photochemical damage to components of the eye. In some instances, the polluting blue light may result in unintended brain stimulation. Red light (and other types of light, such as green light) have been shown to protect the eye from the damage caused by blue light.

PBMT can be used to treat disorders of the eye safely, effectively, and at low cost. Even with its clear advantages, PBMT has not been widely used in the treatment of disorders of the eye. In fact, no personal device exists due to concerns related to safety, personal use, extended use, ergonomics, and portability. Most notably, previous devices have been ineffective at delivery PBMT into the eye. When a patient's eye moves naturally, previous devices have been unable to compensate for this movement, rendering these devices ineffective to deliver the PBMT into the eye. Additionally, previous solutions applying PBMT to a patient's eye have used lasers/light sources to deliver light to the eye without concern for the additional polluting blue light that might enter the patient's eye with the PBMT. While light pollution may be controllable in a clinical setting, the risk of light pollution becomes a large concern when the patient is permitted to apply the PBMT to their own eye in the comfort of their own home. The present disclosure provides a PBMT device that is configured for placement directly over a patient's eye socket to deliver light into the patient's eye, while blocking white light from the environment from entering the patient's eye. In other words, the PBMT device can be opaque to white light so that white light cannot enter the eye during the PBMT. In other instances, the PBMT device can be designed with a lens and/or additional components (such as a Mylar sheet) that filter the blue light out of a light signal being sent to the eye. Additionally, the PBMT device directs the light of PBMT into the patient's eye, no matter if the eye moves.

III. Photobiomodulation Therapy (PBMT)

Photobiomodulation therapy (PBMT) can provide a low-cost and effective alternative or adjunctive treatment for a disorder of the eye. When used on the eye, the light used for PBMT can have one or more wavelengths between 500 nm and 1100 nm and an energy density of 20 mW/cm2 to 75 mW/cm$^2$ applied for a time (e.g., between 30 seconds and 5 minutes). In some instances, two or more wavelengths can be combined for a single PBMT treatment. The unique PBMT device described herein configured to cover a patient's eye socket and direct the light through the pupil and into the eye (regardless of motion of the eye).

The light of PBMT has been shown to have a modulatory effect on retinal cells (including photoreceptors and other cells of the retina, such as support cells) based on the principle that certain molecules in living systems absorb photons and trigger signalling pathways in response to light. When a photon of light is absorbed by a chromophore in a cell, an electron in the chromophore can become excited and jump from a low-energy orbit to a higher-energy orbit. This stored energy then can be used by the living system to perform various cellular tasks. While not wishing to be bound by theory, there is strong evidence to suggest that one of the basic cellular tasks mechanisms of PBMT is the acceleration of electron transfer by electromagnetic radiation in the visible and near infrared region of the spectrum, via the modulation of cytochrome c-oxidase ("CCO") activity in retinal cells. This response is photochemical.

CCO is the primary photo acceptor of visible to near infrared light energy and is the enzyme responsible for catalysing oxygen consumption in cellular respiration and for the production of nitric oxide under hypoxic conditions. High-energy electrons are passed from electron carriers through a series of trans-membrane complexes (including CCO) to the final electron acceptor, generating a proton gradient that is used to produce adenosine triphosphate (ATP). The application of light directly results in ATP production and electron transport. In short, the application of PBMT can increase ATP production, down-regulate cellular respiration modulated by NO, and promotes the metabolism of oxygen, while increasing the production of reactive oxygen species (ROS).

IV. Light Pollution

Light pollution is generally caused by blue light (or blue violet light) having a wavelength less than 455 nm. Blue light exposure causes side effects from mild fatigue and discomfort, resulting in an inability to concentrate, to irreversible photochemical damage, resulting in an increased risk of macular degeneration and vision loss. Laboratory studies have shown that too much exposure to blue light can damage light-sensitive cells in the retina. Outer cone death, accompanied by a fully layer of macrophages and activated microglia has been shown to mediate the blood retinal barrier function impairment by releasing a variety of pro-inflammatory factors, including tumor necrosis factor (TNF) and IL-1. As a result of pro-inflammatory factor release, blood vessels' permeability is increased and some harmful components of the blood (e.g., immune complexes and lymphotoxin) are extruded into the retina.

Unfortunately, like photobiomodulation therapy (PBMT), light pollution also has a photochemical effect on the eye. Mitochondria are the main targets of blue light-associated oxygen free radicals. Under aerobic conditions, blue light stimulates the mechanism of retinal initiation and oxidation, induces a large number of free radicals, destroys messenger ribonucleic acid (mRNA) and proteins, causes necrosis of photoreceptor cells and pigment epithelial cells, and destroys the dynamic balance of the body's normal redox state. Under conditions of severe oxidative stress, the retina ganglion cells (RGCs) present a large number of mitochondria in the intraocular axons and photoreceptors. The macular carotenoids in the Henle layer of the inner layer of the photoreceptor absorb short wave blue light, which occurs between 400 and 480 nm, so that blue light-induced damage to the RGCs' mitochondria is substantial. Extensive receptor interacting protein (RIP)1/RIP3 activation was induces RGC death, thus causing speculation that the RIP kinase inhibitor can be used as a neuroprotector to lessen blue light-induced cell necrosis. The mechanism of light damage to the retina by blue light was labeled as the "bystander effect" because it is triggered by single cell photo-oxidative stress, which induces biological effects in non-targeted cells. Blue light stimulates local oxidative stress in single cells of the retinal pigment epithelium and causes an active ROS-induced signal. The radiation spreads rapidly to the periphery, while the Ca2+ signal was slowly and unevenly transmitted to adjacent cells, which induced changes in the mitochondrial membrane potential. Finally, the metabolic characteristics of the high baseline Ca2+ levels led to localized cell damage in the retinal pigment epithelial cells. In addition, the experimental results showed that blue light could induce degradation of retinal pigments.

The unique PBMT device described herein configured to cover a patient's eye socket (placed directly over the patient's eye socket) to deliver light into a patient's eye (or area surrounding the eye). Notably, the PBMT device can prevent blue light from entering the patient's eye (or area surrounding the eye) by internal components or external opacity. The light reaching the eye can have one or more wavelengths between 500 nm and 1100 nm and an energy density of 20 mW/cm2 to 75 mW/cm$^2$ applied for a time. Additionally, light with wavelengths between 500 nm and 1100 nm, red light and other forms of light like green light, can protect the eye from the effects of blue light. It should be noted that healthy adult eyes are generally able to block blue light, but diseased adult eyes and a child's eyes are generally unable to block the blue light to the extent of a healthy adult eye.

V. Systems

One aspect of the present disclosure can include a system 10 (FIG. 1) that reduces reducing light pollution in PBMT of the patient's eye when directing light into a patient's eye to treat a disorder of the eye. The system 10 includes a controller 12 and a PBMT device 14. The controller 12 can provide power to the PBMT device 14, which can generate the light and can be configured to direct the light into the patient's eye. The PBMT device 14 can be configured for placement directly over a patient's eye socket to deliver light into the patient's eye, while preventing blue light from entering the patient's eye.

The PBMT device 14 can be in the form of a patch, a light bridge, glasses, or the like. The PBMT device may be of different sizes for the type of patient—e.g., a neonate, a child, a small adult, a large adult. Additionally, the PBMT device may be coupled to an anchor, like a strap, to hold the PBMT device in place directly over (e.g., covering) the patient's eye. In some instances, the anchor can secure a unique PBMT device to each of a patient's eyes (such that the unique PBMT devices cover the patient's eyes bilaterally). For example, the PBMT device can be a patch over each eye and connected by a strap.

The controller 12 can provide power to at least a portion of the PBMT device 14, which can generate light when powered. The PBMT device 14 can be shaped to direct the light into (or through) the patient's eye (or an area near the patient's eye). An advantage of the system 10 compared to conventional light delivery solutions is that the PBMT device 14 is configured to direct the light into the patient's eye (or other delivery area) regardless of the orientation of the patient's eye. This allows the patient's eye to receive the benefits of PBMT described above. The system 10 is designed so the patient can receive the PBMT either in the clinic or at home. To this end, the PBMT device 14 can be can be dust tight and waterproof (e.g., at least IP 65).

The PBMT device 14 can include at least a light delivery device 22 that generates the light and a lens 24 that facilitates delivery of the light, as shown in FIG. 2. The lens can contribute to filtering blue light from the light signal. The light signal, in some instances, can be white light. In other instances, the light signal can include a multiplicity of wavelengths. In still other instances, the light signal can include a single wavelength (but may deliver another wavelength at another time). Additionally, at least a portion of the PBMT device 14 can be opaque to white light (portion 26), however this opaqueness is optional. Note that the PBMT device 14 can include additional components to facilitate the delivery of the light through the patient's eye. The PBMT device 14 can be shaped further to ensure delivery of the light through the patient's eye (or to a distinct portion external to the eye, but near the eye, or a non-retinal component of the eye). At least a portion of the lens 24 and/or the light delivery device 22 can be flexible. However, in some instances, at least a portion of the lens 24 and/or the light delivery device 22 can be rigid.

An example of the light delivery device 22 is shown in FIG. 3. The light delivery device 22 can include an array of light delivery devices 34 (e.g., one or more) arranged regularly on a printed circuit board 32. The light delivery devices 34 can be light emitting diodes, laser diodes, or the like. In some instances, the light delivery devices 34 can each (individually) generate light with a wavelength from 500 nm to 1100 nm. In other instances, the light delivery devices 34 can each (individually) generate light with a wavelength from 630 nm to 670 nm or from 800 nm to 900 nm. In other instances, at least one of the light delivery devices 34 can generate white light. The light delivery devices 34 can generate light with a broad spectrum, which may have a multiplicity of wavelengths, and the device can filter blue light from the light signal. The regular arrangement of the light delivery devices 34 with uniform spacing can contribute to the uniform delivery of light (in other words, the light is delivered at a uniform density). Each of the light delivery devices 34 can deliver a unique light signal from a unique position. The printed circuit board 32 can be flexible and/or rigid.

Figure 4:
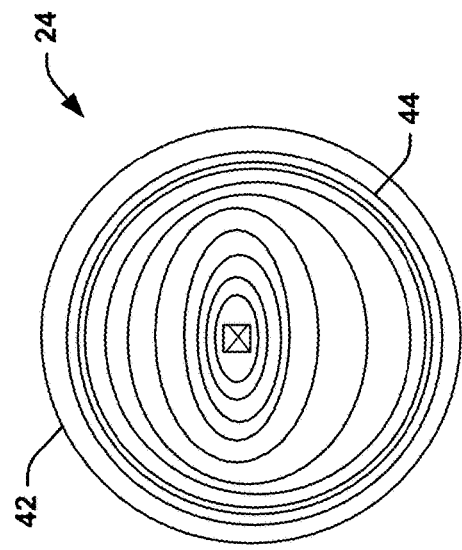
FIG. 4 is a diagram illustration showing an example lens of FIG. 2.

An example of the lens 24 is shown in FIG. 4. The lens 24 can be flexible and can overlay the light delivery device 22 to facilitate delivery of the light through the eye. The lens 24 can include a base 42 and a plurality of ridges 44 that provide a heat sink for the light delivery devices 34. The heat sink absorbs heat from the light delivery devices 34 so that the heat is not transmitted to the eye. At least a portion of the lens 24 can be injected with an antimicrobial or antibacterial element or compound (such as one containing silver). The lens 24 can be constructed of any material that facilitates delivery of light (e.g., silicon, silicone, etc.). The lens can filter at least a portion of blue light from the light signal that reaches the eye (or area surrounding the eye).

The controller 12 of system 10 can deliver power according to a wired connection and/or a wireless connection. The controller 12 can include an internal battery and/or external power receiver/storage to provide power to at least a portion of the electronics of the PBMT device 14 required for operation of the system 10. In some instances, the controller 12 can be a unit external to the PBMT device 14 (e.g., similar to a TENS device). In other instances, the controller 12 can be included with the PBMT device 14 (e.g., in the periphery of the PBMT device 14). In still other instances, the controller 12 can be located on or within a device proximal to the PBMT device (e.g., a strap device).

The controller 12 can receive and/or provide AC and/or DC current. Notably, the controller can include a log generator that is only accessible to previously approved users (e.g., a doctor or hospital). The previously approved users can be associated with user names associated with permissions that allow access to the logs. However, the logs can be transmitted to computers associated with the permitted users. The logs can include data related to user of the PBMT—such as when, where, how often, and the like.

Figure 5:
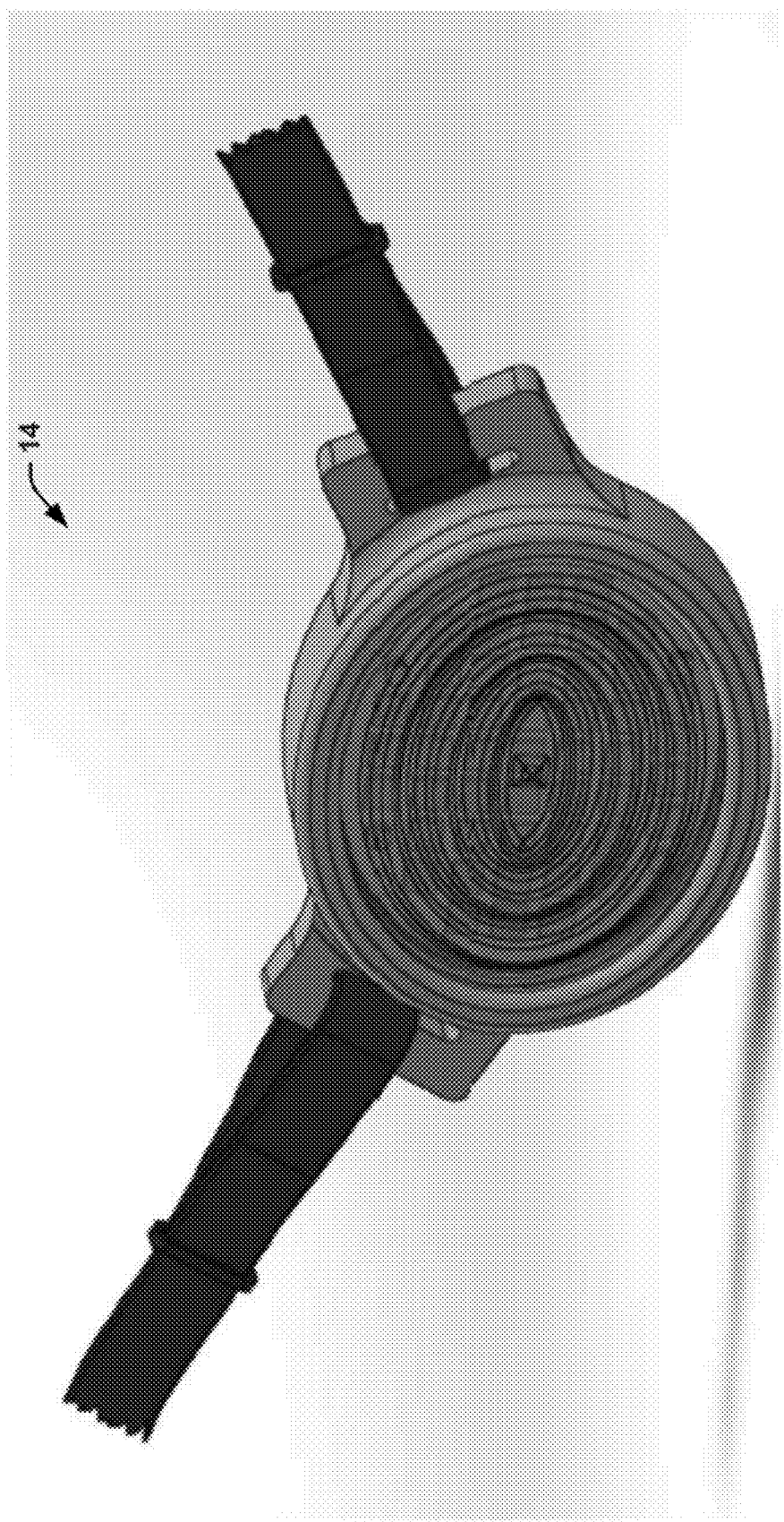
FIG. 5-6 illustrate an example device that can be used to implement the system of FIG. 1.
Figure 6:
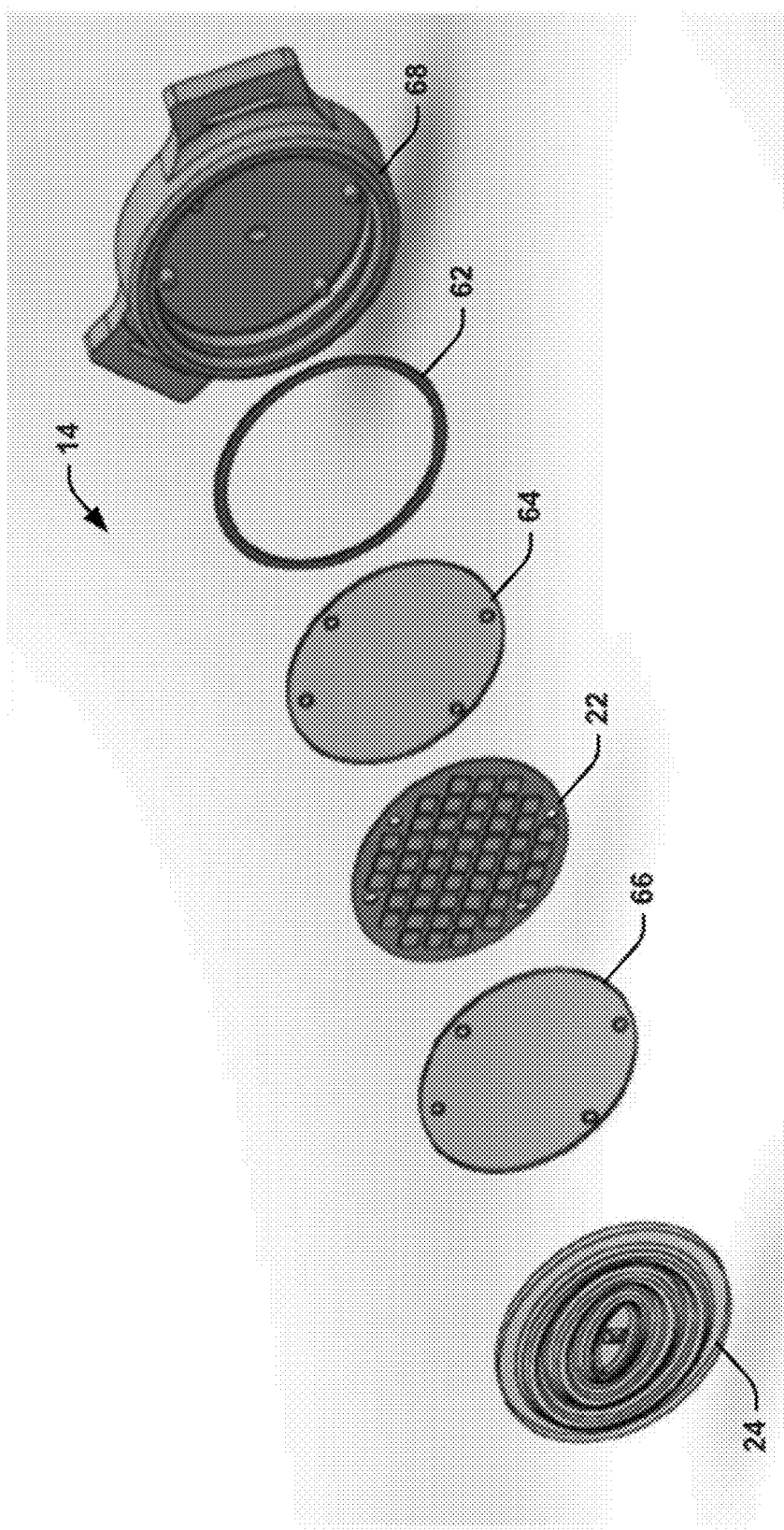

FIGS. 5 and 6 provide an illustration of an example PBMT device 14 that can be used in the system 10. FIG. 5 provides a view from an eye looking through the lens to receive the PBMT. This PBMT device 14 can include a strap to anchor the device in position over the eye. FIG. 6 shows the components of the device shown in FIG. 5. The lens 24 (shaped to conform to the eye socket, made of silicon with concentric rings, and configured to remove blue light from a light signal) and the light delivery device 22 (flexible design), also referred to as a printed circuit board, are separated by a Mylar layer 66 made of a Mylar sheet to further facilitate the homogeneous, uniform density of light (to facilitate diffusion of the light). Another Mylar layer 64 is located behind the light delivery device 22 (to filter blue light from the light signal) between the light delivery device 22 and the housing component 68. The device also includes a flexible metallic ring 62 to conform the lens 24 and the light delivery device 22 to a shape of the patient's eye to direct the light through the patient's eye and into the patient's pupil. The device also includes a housing component 68 to anchor the layers therewithin. In some instances, the housing component 68 can be opaque to white light, blocking external white light from entering the eye during the PBMT and any time that the device 14 covers the eye). As shown in FIGS. 5 and 6, the housing component 68 can mate with the anchor (in this case the strap). Moreover, the opacity of the housing component 68 can better focus the light into the patient's eye. Each of the layers 24, 66, 22, and 64 can include holes to attach to pegs within the housing component 68.

As noted, the one or more Mylar layers 64 is located behind the light delivery device 22 between the light delivery device 22 and the housing component 68 of the PBMT device. The Mylar layers 64 can work as a blue light filter. When the light delivery device 22 delivers white light (or other types of light including multiple wavelengths), the Mylar layer 64 can provide a filter for the white light (or other types of light including multiple wavelengths), ensuring that blue light does not reach the patient's eye. Filtering the blue light from the white light (or other types of light including multiple wavelengths) so that blue light, which can be damaging to the patient's eye, does not reach the patient's eye. Therefore, white light can be applied (from one or more diodes that produce white light) without blue light reaching the patient's eye.

In addition to the one or more Mylar layers 64 or as an alternative to the Mylar layers 64, a blue light filtering material can be used (in the same position as the one or more Mylar layers 64, but could be in a different position than the one or more Mylar layers 64). The blue light filtering material can filter out the blue light from the white light (or other types of light including multiple wavelengths). For example, Mylar works by distributing light as it scatters red light and may not filter out the entirety of the blue light; the blue light filtering material can ensure that the blue light within the white light (or other types of light including multiple wavelengths) is eliminated from the white light (or other types of light including multiple wavelengths). As another example, the blue light filtering material can replace the Mylar layers 64 to ensure that the blue light is removed from the white light (or other types of light including multiple wavelengths).

VI. Methods

Figure 7:
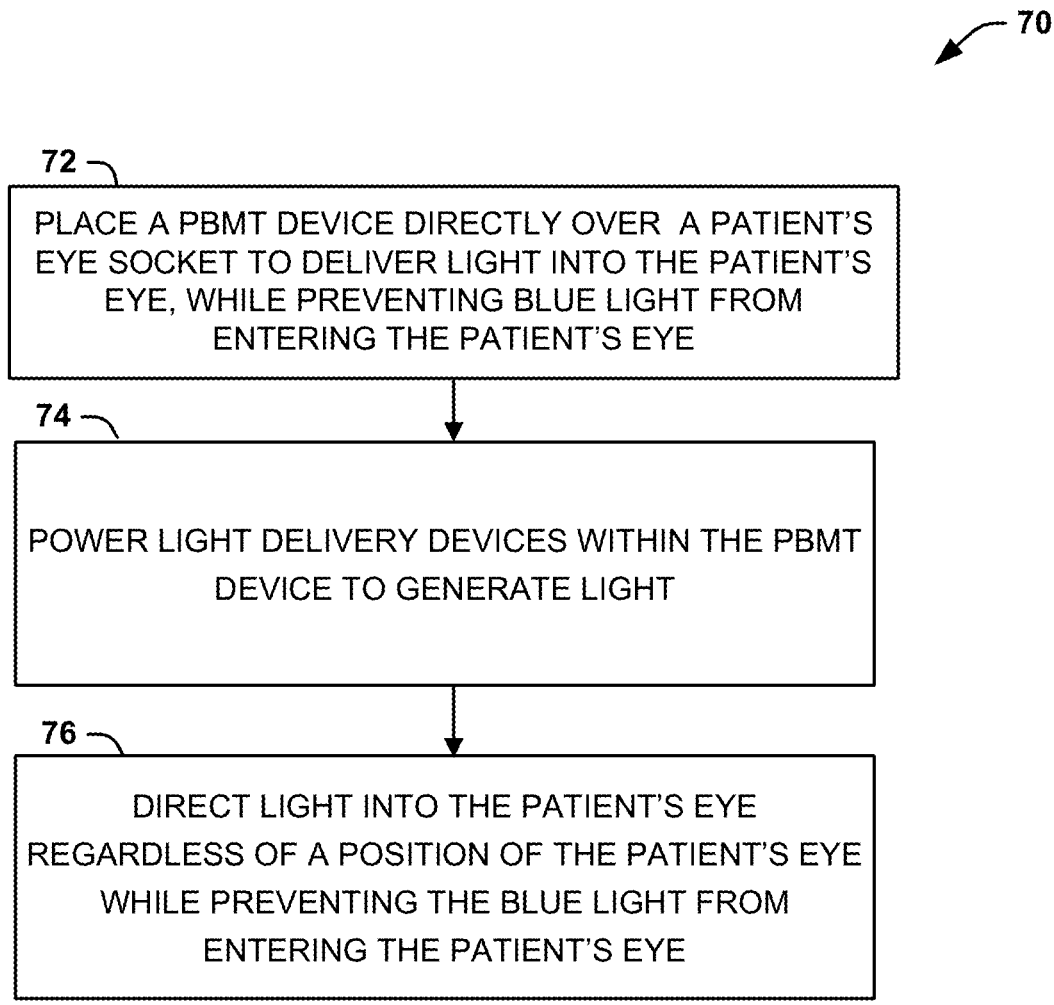
FIG. 7 is a process flow diagram of an example method for reducing light pollution in PBMT of the patient's eye when directing light into a patient's eye to treat a disorder of the eye in accordance with another aspect of the present disclosure.

Another aspect of the present disclosure can include a method 70 (FIG. 7 for reducing light pollution in PBMT of the patient's eye when directing light into a patient's eye to treat a disorder of the eye. The method 70 can be executed by hardware—for example, at least a portion of the system 10 shown in any one of FIGS. 1-6 and described above.

The method 70 is illustrated as process flow diagram with flowchart illustrations. For purposes of simplicity, the method 70 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 70. Additionally, one or more elements that implement the methods 70, such as PBMT device 13, the controller 12 of FIG. 1, may include a non-transitory memory and one or more processors that can facilitate the configuration and generation of the light of PBMT.

At step 72, a PBMT device can be placed directly over a patient's eye socket to deliver light into the patient's eye, while preventing blue light from entering the patient's eye. The lens of the PBMT device can be configured to filter the blue light from a light signal. Additionally or alternatively, a Mylar sheet (e.g., Mylar sheet 64) located between the housing of the PBMT device and the printed circuit board can be configured to remove blue light from the light signal. Additionally or alternatively, at least a portion of the PBMT device can be opaque to white light (e.g., opaque elements 26 or 68). As one example, the PBMT device can be in the form of an eye patch (e.g., shown in FIGS. 5 and 6). However, the PBMT device can take the form of one or more different examples, such as glasses, goggles, a light bridge, or any other device that can be placed in over the patient's eye socket. The PBMT device can also include a mechanism to hold the PBMT device in place, like a strap (which may be used to hold two PBMT devices in place over each of a patient's eye).

The PBMT device can be dust tight and waterproof (e.g., at least IP 65). The PBMT device can include a printed circuit board, having an array of light delivery devices. The printed circuit board can be flexible and/or rigid. The array of light delivery devices can deliver light at a uniform density. The light delivery devices are light emitting diodes and/or laser emitting diodes. The light delivery devices can each provide light with a wavelength from 500 nm to 1100 nm (which may switch over time). As a more specific example, the light delivery devices can each provide light with a wavelength from 630 nm to 670 nm or 800 nm to 900 nm. As an alternative, one or more of the light delivery devices can provide white light. It should be noted that certain wavelengths of light can neutralize blue light, such as red light or green light.

The PBMT can also include a lens, laid over the PBMT device, having a plurality of ridges that provide a heat sink for the light delivery devices and can provide some filtering of blue light. In some instances, the PBMT device can include a flexible metallic ring to conform the printed circuit board and/or the lens to direct the light through the patient's eye into the patient's eye into the patient's pupil. Additionally or alternatively, the PBMT can include at least one Mylar sheet (e.g., located between the lens and the printed circuit board and/or between the printed circuit board and the housing portion) to further facilitate the homogeneous uniform density of light and/or filter blue light.

At step 74, light delivery devices within the PBMT device can be powered to generate light. The power can be supplied by a controller device. When powered, the light delivery devices can generate the light. The light can be delivered for a predetermined time (e.g., from 30 seconds-5 minutes). Notably, the light delivery devices are arranged on the printed circuit board to enable the uniform density of light. The power can be provided by the controller device, which can receive and/or supply AC and/or DC current. The controller can include a power source (e.g., a battery, such as a rechargeable battery). In some instances, the controller can include a data mining capability to populate a log generator to record when, where, and how often the patient utilizes the PBMT device.

At step 76, the light can be directed into the patient's eye regardless of a position of the patient's eye while preventing blue light from entering the patient's eye. As an example, the one or more Mylar layers can be located behind the light delivery device 22 between the light delivery device 22 and the housing component 68 of the PBMT device. These Mylar layers can work as a blue light filter. When the light delivery device 22 delivers white light (or other types of light including multiple wavelengths), these Mylar layers can provide a filter for the white light (or other types of light including multiple wavelengths), ensuring that blue light does not reach the patient's eye. Filtering the blue light from the white light (or other types of light including multiple wavelengths) so that blue light, which can be damaging to the patient's eye, does not reach the patient's eye. Therefore, white light can be applied (from one or more diodes that produce white light) without blue light reaching the patient's eye. In addition to the one or more Mylar layers 64 or as an alternative to the Mylar layers 64, a blue light filtering material can be used (in the same position as the one or more Mylar layers 64, but could be in a different position than the one or more Mylar layers 64). The blue light filtering material can filter out the blue light from the white light (or other types of light including multiple wavelengths). For example, Mylar works by distributing light as it scatters red light and may not filter out the entirety of the blue light; the blue light filtering material can ensure that the blue light within the white light (or other types of light including multiple wavelengths) is eliminated from the white light (or other types of light including multiple wavelengths). As another example, the blue light filtering material can replace the Mylar layers 64 to ensure that the blue light is removed from the white light (or other types of light including multiple wavelengths). As another example (as an alternative or in addition to the filter), the housing can be opaque to white light.

The uniform distribution of light ensures that the proper dose of light travels through the pupil. In fact, the uniform distribution of light ensures that light enters through the pupil regardless of the orientation of the patient's eye.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A system comprising:
    a photobiomodulation therapy (PBMT) device configured for placement directly over a patient's eye socket to deliver light with a homogeneous uniform density into the patient's eye, while preventing blue light from entering the patient's eye;
    a controller configured to power the PBMT device, wherein the PBMT device comprises:
        a printed circuit board comprising an array of light delivery devices arranged with a uniform spacing to provide the light, wherein the printed circuit board is powered by the controller; and
        a lens comprising a plurality of ridges that provide a heat sink for the light delivery device, wherein the lens delivers the light into the patient's eye.

2. The system of claim 1, wherein the array of light delivery devices comprise light emitting diodes or laser diodes.

3. The system of claim 2, wherein at least one of the light delivery devices provides white light.

4. The system of claim 3, further comprising at least one MYLAR sheet located between the printed circuit board and a housing of the PBMT device, wherein the at least one MYLAR sheet filters the blue light from the white light and prevents the blue light from entering the eye.

5. The system of claim 4, wherein the PBMT device further comprises at least one other MYLAR sheet to facilitate a homogeneous uniform density of light from the light delivery devices, wherein the at least one other MYLAR sheet is located between the printed circuit board and the lens.

6. The system of claim 2, wherein each of the light delivery devices provides light with at least one wavelength from 500 nm to 1100 nm.

7. The system of claim 6, wherein the PBMT device blocks the blue light that is part of white light from the surrounding environment from entering the patient's eye due to an opacity of the PBMT device.

8. The system of claim 1, wherein an antimicrobial material is embedded within the lens.

9. The system of claim 1, wherein the PBMT device further comprises a flexible metallic ring to conform the printed circuit board and the lens to the patient's eye socket.

10. The system of claim 9, wherein the flexible metallic ring enables the PBMT device to direct the light through the patient's eye and into the patient's pupil.

11. The system of claim 1, wherein the PBMT device comprises an eyepatch device configured to attach to the patient's head to cover the patient's eye.

12. The system of claim 1, wherein the controller is at least one of built into the PBMT device, housed in a strap in proximity to the PBMT device, or external to the PBMT device.

13. The system of claim 1, wherein the controller comprises a power source, a non-transitory memory, and a processor, and communicates with the PBMT device according to a wired connection or a wireless connection.

14. The system of claim 1, further comprising a second PBMT device connected to the PBMT device, wherein the second PBMT device is configured to cover another eye of the patient.

15. The system of claim 1, wherein the PBMT device is dust tight and waterproof.

16. A method comprising:
    placing a photobiomodulation therapy (PBMT) device directly over a patient's eye socket to deliver light into the patient's eye, while preventing blue light from entering the patient's eye, wherein the PBMT device comprises:
        a printed circuit board comprising an array of light delivery devices arranged with a uniform spacing to provide the light; and
        a lens comprising a plurality of ridges that provide a heat sink for the light delivery device;
    powering the array of light delivery devices of the PBMT device to generate light by a controller; and
    directing the light with a homogeneous uniform density into the patient's eye regardless of a position of the patient's eye while preventing the blue light from entering the patient's eye.

17. The method of claim 16, wherein the PBMT device further comprises:
    a flexible metallic ring to conform the printed circuit board and the lens to the patient's eye and to direct the light through the patient's eye and into the patient's pupil; and
    at least one MYLAR sheet configured to filter the blue light from the light as and/or before the blue light is directed to the patient's eye.

18. The method of claim 17, wherein the at least one MYLAR sheet is between the printed circuit board and a housing of the PBMT device.

19. The method of claim 16, wherein the light comprises white light.

* * * * *